United States Patent [19]
Pudas

[11] Patent Number: 5,886,216
[45] Date of Patent: Mar. 23, 1999

[54] METHOD FOR PRODUCING A CHEMICAL PRODUCT

[75] Inventor: Roland Pudas, Nödinge, Sweden

[73] Assignee: EKA Chemicals AB, Bohus, Sweden

[21] Appl. No.: 791,144

[22] Filed: Jan. 30, 1997

[30] Foreign Application Priority Data

Jan. 31, 1996 [SE] Sweden .................................. 9600347

[51] Int. Cl.$^6$ ...................... C07C 407/00; C07C 409/26; A01N 37/16
[52] U.S. Cl. ........................ 562/6; 562/2; 562/4; 514/557
[58] Field of Search ................................. 514/557; 562/2, 562/4, 6

[56] References Cited

U.S. PATENT DOCUMENTS 3,264,346  8/1966  Weiberg ...................................... 562/6

FOREIGN PATENT DOCUMENTS 1432773  2/1966  France .
949094  8/1960  United Kingdom .

Primary Examiner—John Pak
Attorney, Agent, or Firm—McDermott, Will & Emery

[57] ABSTRACT

The invention relates to a method for producing peracetic acid by reacting hydrogen peroxide and acetic acid in a water-based reaction medium in a reactor and continuously distilling off the produced peracetic acid. Thermal energy in an in an amount exceeding about 0.2 kW/kg reaction medium.

20 Claims, 1 Drawing Sheet

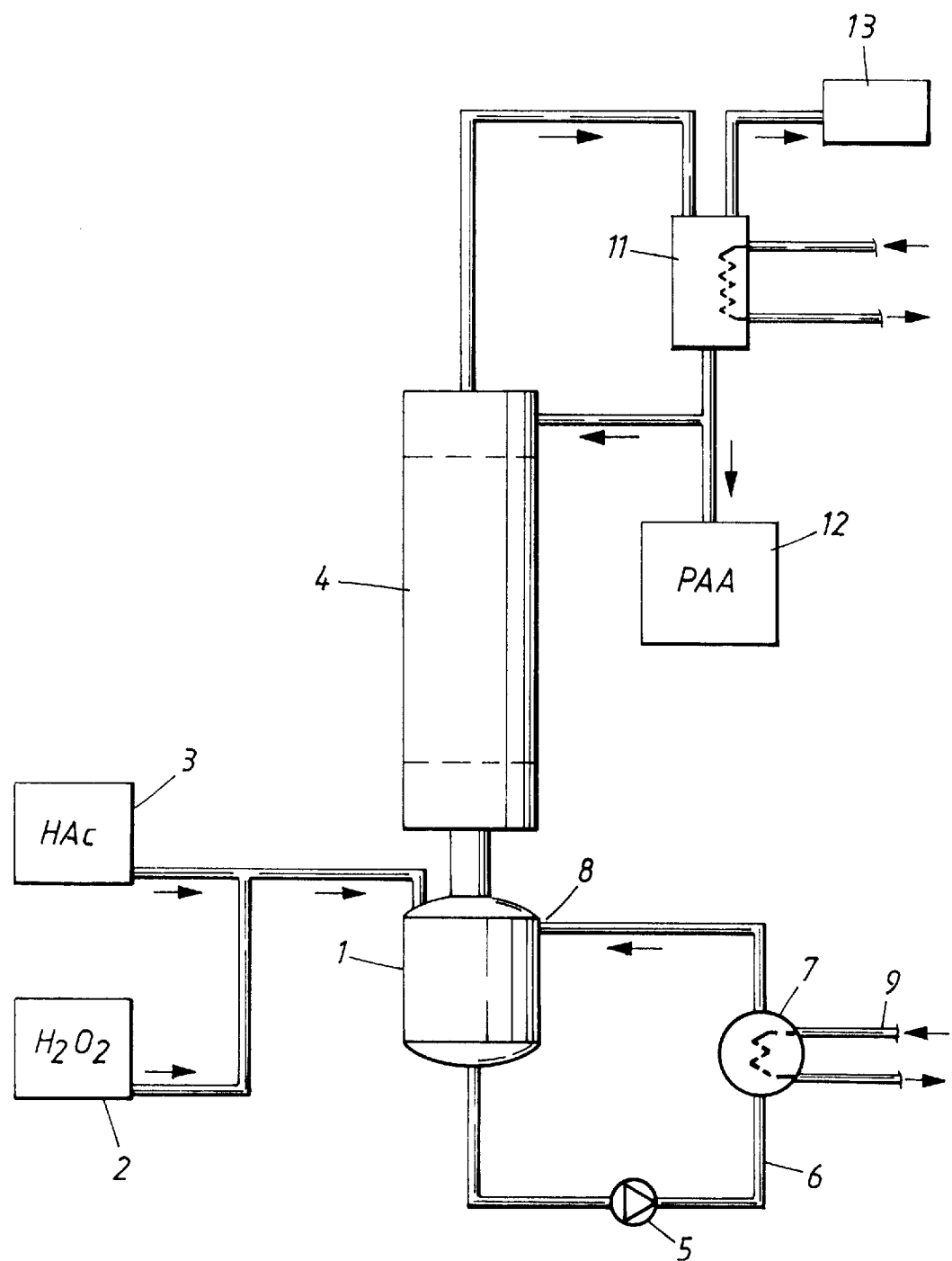

METHOD FOR PRODUCING A CHEMICAL PRODUCT

BACKGROUND OF THE INVENTION

The present invention relates to a method for producing peracetic acid by reacting hydrogen peroxide and acetic acid in a aqueous reaction medium, from which peracetic acid is continuously distilled off.

Peracetic acid in aqueous solution can be used as disinfectant or for bleaching various materials and is especially suited for environment-friendly bleaching of cellulose pulp. Prior-art production processes, however, are not sufficiently efficient to be of commercial interest.

GB Patent 949,094 discloses the production of peracetic acid by distilling off peracetic acid from a reaction medium containing acetic acid, hydrogen peroxide, peracetic acid and sulphuric acid in equilibrium. However, the described process has a production rate of only about 1 g peracetic acid per kg reaction medium and minute.

D. Swern, "Organic Peroxides", Vol. 1, John Wiley & Sons, New York 1970, pp 349–351, describes a similar process, but mentions no production rates.

The present invention concerns a solution to the problem of providing an efficient process for producing peracetic acid from acetic acid and hydrogen peroxide in aqueous phase, the product preferably containing as little impurities as possible, for instance of acetic acid. Since peracetic acid easily decomposes, both safety problems and high investment costs for the process equipment will arise for large volumes of reaction medium, and therefore it is desirable to achieve a high production rate in relation to the amount of reaction medium.

SUMMARY OF THE INVENTION

According to the invention, it has been found that a high production rate can be achieved if the reaction medium is continuously supplied with a comparatively large amount of thermal energy from outside, although the reaction between acetic acid and hydrogen peroxide in itself is exothermic.

Thus, the invention relates to a method for producing peracetic acid by reacting hydrogen peroxide and acetic acid in a aqueous reaction medium in a reactor and continuously distilling off produced peracetic acid, the reaction medium being continuously supplied with thermal energy in an amount exceeding about 0.2 kW/kg reaction medium, most preferred exceeding about 0.5 kW/kg reaction medium. Preferably, thermal energy is supplied to the reaction medium in an amount from about 0.5 to about 5 kW/kg, especially from about 0.8 to about 5 kW/kg, most preferred from about 1 to about 3 kW/kg.

A distillation column is suitably connected directly to the reactor, in which the reaction medium is maintained at the boiling point. Since peracetic acid and hydrogen peroxide are sensitive to high temperatures, the distillation suitably takes place at a pressure below atmospheric pressure, and preferably a pressure in the reactor from about 40 to about 250 mbar, especially from about 60 to about 150 mbar is maintained. The temperature in the reactor preferably is from about 30° to about 65° C., especially from about 40° to about 55° C.

It has appeared to be possible to add sufficiently great amounts of heat to the reaction medium at the same time as the decomposition of peracetic acid and hydrogen peroxide is minimised by causing the reaction medium in the reactor to circulate through a device for heating thereof, preferably by heat exchange against hot water, the temperature of the medium after heating suitably not exceeding the temperature in the reactor by more than about 30° C., preferably by no more than about 20° C., most preferred by no more than about 15° C. The temperature of the reaction medium immediately after heating suitably is from about 5 to about 15° C. higher than in the reactor, preferably from about 8° to about 12° C. higher than in the reactor. Preferably, the temperature of the heated reaction medium in the circulation loop does not exceed about 80° C., most preferred not about 70° C. In order to obtain a sufficient supply of energy to the reactor, the reaction medium suitably circulates through the heating device at a flow rate so as to be circulated in the reactor from about 30 to about 200 times per hour, preferably from about 70 to about 150 times per hour. Suitably, the pressure in the circulation loop is higher than in the reactor, the reaction medium in the loop being heatable without reaching the boiling point at the prevailing pressure.

The reaction medium in the reactor suitably contains from about 3 to about 12% by weight, preferably from about 4 to about 8% by weight of peracetic acid, suitably from about 1 to about 8% by weight, preferably from about 2 to about 6% by weight of acetic acid, and suitably from about 10 to about 35% by weight, preferably from about 20 to about 30% by weight of hydrogen peroxide. Preferably, the molar ratio of hydrogen peroxide to acetic acid is from about 4:1 to about 30:1, most preferred from 6:1 to about 25:1. A peracetic acid concentration that is less than the equilibrium concentration is suitably maintained in the reaction medium, which has been found to increase the production rate. Suitably, the reaction medium also contains an acid catalyst, preferably one or more mineral acids in an amount from about 10 to about 25% by weight, most preferred from about 15 to about 20% by weight. Examples of usable mineral acids are sulphuric acid and phosphoric acid. To reduce the decomposition of peracetic acid and/or hydrogen peroxide, the reaction medium suitably also contains one or more stabilisers such as phosphonic acids or salts thereof and/or dipicolinic acid or derivatives thereof. Usable phosphonic acids include e.g. 1-hydroxyethylidene-1,1-diphosphonic acid, 1-aminoethane-1,1-diphosphonic acid, aminotri-(methylene phosphonic acid), ethylenediamine-tetra (methylene phosphonic acid), hexamethylenediamine-tetra (methylene phosphonic acid), diethylenetriamine-penta (methylene phosphonic acid), diethylenetriamine-hexa (methylene phosphonic acid), dimethylamino methanediphosphonic acid, aminoacetic acid-N,N-dimethylene phosphonic acid, 3-aminopropane-1-hydroxy-1,1-diphosphonic acid, 2-phosphonobutane-1,2,4-tricarboxylic acid, phosphonosuccinic acid, 1-phosphono-1-methylsuccinic acid and 1-amino-phenylmethane diphosphonic acid.

During the course of the process, hydrogen peroxide in the form of an aqueous solution as well as acetic acid are suitably supplied continuously to the reactor, while an aqueous solution of peracetic acid is distilled off. The remaining components in the reaction medium are added when starting and remain therein since they are neither chemically consumed nor do they accompany the distillate. However, it may be suitable to continuously add a stabiliser in order to compensate for any decomposition thereof. Since any impurities in the raw materials can be concentrated in the reaction medium, it may also be convenient to have a continuous bleed of reaction medium or alternatively exchange the entire quantity thereof regularly.

BRIEF DESCRIPTION OF THE DRAWINGS

The invention will now be described in more detail with reference to the accompanying FIGURE which schematically illustrates a process for producing peracetic acid. However, the invention is not restricted to the embodiment shown, but only by the scope of the claims.

A reactor 1 holds a reaction medium which is formed from an aqueous solution containing hydrogen peroxide ($H_2O_2$), acetic acid (HAc), peracetic acid (PAA), a mineral acid such as sulphuric acid, and a stabiliser such as a phosphonic acid. The reactor 1 is continuously supplied with an aqueous solution of hydrogen peroxide from a tank 2 and acetic acid from a tank 3. A subatmospheric pressure and a temperature sufficient for peracetic acid and water to be withdrawn through the distillation column 4 prevail in the reactor 1, which normally implies that the reaction medium is boiling.

The temperature in the reactor is maintained by circulating the reaction medium with the aid of a pump 5 in a loop 6 through a heat exchanger 7, where it is heated by means of hot water 9, before being recycled to the reactor 1 through an inlet 8. No reflux boiling takes place, but the pump 5 increases the pressure, and the inlet 8 is so adapted that an substantial part of the pressure drop occurs above the inlet, the pressure in the circulation loop 6 and the heat exchanger 7 thereby being so high that no boiling takes place in spite of the temperature increase which preferably is less than 12° C. Preferably, the reaction medium is circulated in the reactor from 70 to 150 times per hour through the circulation loop 6 and the heat exchanger 7, thereby making it possible to supply great amounts of thermal energy to the reactor 1 without the decomposition of peracetic acid or hydrogen peroxide becoming unacceptably great.

In the distillation column 4, the peracetic acid is separated from the other components in the reaction medium, and an aqueous solution of from about 30 to about 50% by weight peracetic acid suitably containing less than about 5% by weight, preferably less than about 2% by weight of acetic acid and most preferred being substantially free from hydrogen peroxide and mineral acid is caused to condense in a condenser 11. Part of the condensate is conducted to a product tank 12 while the remainder is recycled to the distillation column 4. A vacuum source 13 is connected to the condenser such that a suitable subatmospheric pressure prevails in the column 4 and the reactor 1. To the top of the distillation column 4, a stabiliser can be supplied, for instance one of the above-mentioned phosphonic acids or a salt thereof, part of the stabiliser accompanying the product to the tank 12 while the remainder is conveyed downwards and distributed in the column 4 and the reactor 1.

The process equipment, such as reactor, distillation column, piping, heat exchangers, tanks, etc., are suitably made of a corrosion-proof material such as aluminium or stainless steel, for instance SS 2343, 2353, 2304, 2305, 254 SMO or Hasteloy™. Other usable materials are tantalum, glass or vitreous enamel, impregnated graphite, fluoroplastics, such as PTFE, PVDF, PFA or FEP, fluoroplastic-coated materials, polyethylene, polypropylene, siliceous carbide or ceramic materials.

DETAILED DESCRIPTION OF THE PREFERRED EMBODIMENTS

The invention will be illustrated in detail in the following Example. Unless otherwise indicated, all contents relate to % by weight.

EXAMPLE

In a plant according to the enclosed Figure, the reaction medium in the reactor 1 was an aqueous solution of 22% hydrogen peroxide, 6% acetic acid, 7% peracetic acid, 16% sulphuric acid and 1% stabiliser in the form of 1-hydroxyethylidene-1,1-diphosphonic acid. The pressure in the reactor 1 was 80 mbar, while the temperature was 48° C. The reaction medium was circulated 90 times per hour through the circulation loop 6 and the heat exchanger 7, its temperature being increased by 10° C. before flashing at the inlet 8 of the reactor. As a result, 1 kW thermal energy per kg reaction medium was supplied. Hydrogen peroxide in the form of a 50% aqueous solution and acetic acid was supplied continuously, while a product substantially consisting of an aqueous solution of 40% peracetic acid and containing less than 1% acetic acid was obtained after the condenser 11. In a stationary state, the production rate was about 6 g peracetic acid per kg reaction medium and minute, while the yield was about 99% based on the supplied amount of hydrogen peroxide.

I claim:

1. A method for producing peracetic acid comprising reacting hydrogen peroxide and acetic acid in a aqueous reaction medium in a reactor, continuously distilling off produced peracetic acid, and continuously supplying the reaction medium with thermal energy in an amount exceeding about 0.2 KW/kg reaction medium.

2. A method as claimed in claim 1, wherein the reaction medium is continuously supplied with thermal energy in an amount exceeding about 0.5 kW/kg reaction medium.

3. A method as claimed in claim 2, wherein the reaction medium is continuously supplied with thermal energy in an amount from about 0.8 to about 5 kW/kg.

4. A method as claimed in claim 1, wherein the reaction medium in the reactor is supplied with heat by causing it to circulate through a device for heating.

5. A method as claimed in claim 4, wherein the pressure in the circulation loop exceeds the pressure in the reactor, and the reaction medium in the circulation loop is heated to a temperature below the boiling point at the prevailing pressure.

6. A method as claimed in claim 4 or 5, wherein the circulating reaction medium is heated to an extent that its temperature, after heating, does not exceed the temperature in the reactor by more than about 20° C.

7. A method as claimed in claim 6, wherein the temperature of the reaction medium after heating does not exceed the temperature in the reactor by more than about 15° C.

8. A method as claimed in claim 4, wherein the temperature of the heated reaction medium in the circulation loop does not exceed about 80° C.

9. A method as claimed in claim 8, wherein the temperature of the heated reaction medium in the circulation loop does not exceed about 70° C.

10. A method as claimed in claim 4, wherein the reaction medium in the reactor circulates through the heating device at a rate of flow so as to be circulated from about 70 to about 150 times per hour.

11. A method as claimed in claim 1, wherein the molar ratio of hydrogen peroxide to acetic acid in the reaction medium is from about 4:1 to 30:1.

12. A method as claimed in claim 1, wherein the peracetic acid concentration in the reaction medium is less than the equilibrium concentration.

13. A method as claimed in claim 1, wherein the distillation results in a product substantially consisting of an aqueous solution containing from about 30 to about 50% by weight peracetic acid and less than about 2% by weight acetic acid.

14. A method as claimed in claim 2, wherein the reaction medium in the reactor is supplied with heat by causing it to circulate through a device for heating.

15. A method as claimed in claim 3, wherein the reaction medium in the reactor is supplied with heat by causing it to circulate through a device for heating.

16. A method as claimed in claim 14, wherein the pressure in the circulation loop exceeds the pressure in the reactor, and the reaction medium in the circulation loop is heated to a temperature below the boiling point at the prevailing pressure.

17. A method as claimed in claim 15, wherein the pressure in the circulation loop exceeds the pressure in the reactor, and the reaction medium in the circulation loop is heated to a temperature below the boiling point at the prevailing pressure.

18. A method as claimed in claim 5, wherein the circulating reaction medium is heated to an extent that its temperature, after heating, does not exceed the temperature in the reactor by more than about 20° C.

19. A method as claimed in claim 5, wherein the temperature of the reaction medium after heating does not exceed the temperature in the reactor by more than about 15° C.

20. A method as claimed in claim 5, wherein the temperature of the heated reaction medium in the circulation loop does not exceed about 80° C.

* * * * *